United States Patent [19]

Eng

[11] 4,401,653

[45] Aug. 30, 1983

[54] COMBINATION OF RAPAMYCIN AND PICIBANIL FOR THE TREATMENT OF TUMORS

[75] Inventor: Chee P. Eng, Dollard des Ormeaux, Canada

[73] Assignee: Ayerst, McKenna & Harrison Inc., Montreal, Canada

[21] Appl. No.: 241,867

[22] Filed: Mar. 9, 1981

[51] Int. Cl.³ ............................................. A61K 35/00
[52] U.S. Cl. .................................................... 424/114
[58] Field of Search ........................................ 424/114

[56] References Cited

U.S. PATENT DOCUMENTS

| | | | |
|---|---|---|---|
| 3,477,914 | 11/1969 | Okamota et al. | 424/93 |
| 3,632,746 | 1/1972 | Kono et al. | 424/93 |
| 3,929,992 | 12/1975 | Sehgal et al. | 424/122 |
| 3,993,749 | 11/1976 | Sehgal et al. | 424/122 |

FOREIGN PATENT DOCUMENTS 877700  1/1980  Belgium ............................. 424/122

OTHER PUBLICATIONS

C. Vezina et al., J. Antibiot., 28, 721 (1975).
S. N. Sehgal et al., J. Antibiot., 28, 727 (1975).
H. Baker et al., J. Antibiot., 31, 539 (1978).
R. R. Martel et al., Can. J. Physiol. Pharmacol., 55, 48 (1977).
T. Aoki et al., J. Natl. Cancer Inst., 56, 687 (1976).
An English translation of I. Kimura, Gan-to-Kagaku-Ryoho (Cancer and Chemotherapy), 2, 21 (1975).
An English translation of T. Hattori, J. Japan Soc. Cancer Therapy, 9, 381 (1974).
An English translation of I. Kimura et al., Gan-no-Rinsho (Japan J. Cancer Clin.) 18,886 (1972).
Host Defense Stimulator, Anti-Tumor·Str. Pyogenes Preparation, Picibanil (OK-432), Chugai Pharmaceutical Co. Ltd., Tokyo, Japan, 1975.

*Primary Examiner*—Jerome D. Goldberg
*Attorney, Agent, or Firm*—Arthur E. Wilfond

[57] ABSTRACT

Described is a method of using a combination of rapamycin and picibanil for the treatment of transplantable carcinogenic tumors.

4 Claims, No Drawings

COMBINATION OF RAPAMYCIN AND PICIBANIL FOR THE TREATMENT OF TUMORS

BACKGROUND OF THE INVENTION

This invention relates to methods of using a combination of rapamycin and picibanil for the treatment of transplantable carcinogenic tumors.

Rapamycin is an antifungal antibiotic described by C. Vezina et al., J. Antibiot., 28, 721 (1975),, S. N. Sehgal et al., J. Antibiot., 28, 727 (1975), S. N. Sehgal et al., U.S. Pat. No. 3,929,992, issued Dec. 30, 1975 and S. N. Sehgal et al., U.S. Pat. No. 3,993,749, issued Nov. 23, 1976. The latter two patents are herein incorporated by reference. Rapamycin is extracted from a streptomycete (*Streptomyces hydroscopicus*) isolated from an Easter Island soil sample and is particularly effective against *Candida albicans* both in vitro and in vivo, H. A. Baker et al., J. Antibiot., 31, 539 (1978). A report by R. R. Martel et al., Can. J. Physiol., 55, 48 (1977) describes the use of rapamycin for the prevention of the development of experimental immunopathies. Recently, rapamycin was shown to be an effective agent for treating carcinogenic tumors in a mammal by S. N. Sehgal and C. Vezina, U.S. patent application Ser. No. 957,626, filed Nov. 3, 1978, herein incorporated by reference. In Belgium, a corresponding application of the latter application issued as Belgium Pat. No. 877,700 on Jan. 14, 1980.

Picibanil (also referred to under the code names, OK-432 and PC-B-45) is an anti-malignant tumor agent with the distinctive feature of potentiating host defense functions against malignancy. Picibanil is produced by incubating the culture of the low virulent Su strain of type III, group A *Streptococcus pyogenes* of human origin in Bernheimer's Basal Medium with added penicillin G potassium followed by lyophilization of the incubation mixture, T. Aoki et al., J. Natl. Cancer Inst., 56, 687 (1976); H. Okamota et al., U.S. Pat. No. 3,477,914, issued Nov. 11, 1969, and T. Kono et al., U.S. Pat. No. 3,632,746, issued Jan. 4, 1972. In addition to its use as a single agent for the treatment of some tumors, picibanil has been reported to have been combined with other anticancer agents. The following reports are illustrative thereof, I. Kimura, Gan-to-Kagaku-Ryaho (Cancer and Chemotherapy), 2, 21 (1975); T. Hattori, J. Japan Soc. Cancer Therapy, 9, 381 (1974); I. Kimura et al., Gan-no-Rinsho (Japan J. Cancer Clin.) 18, 886 (1972); and Host Defense Stimulator, Anti-Tumor Str. Pyogenes Preparation, PICIBANIL (OK-432), 1975, Chugai Pharmaceutical Co. Ltd., Tokyo, Japan.

The combination of rapamycin with picibanil for the treatment of transplantable tumors is novel. The combination of the agents affords a much more effective form of antitumor therapy than that provided by giving the agents alone.

SUMMARY OF THE INVENTION

According to this invention a method is provided for treating transplantable tumors in a mammal, which comprises administering to the mammal an anti-transplantable tumor effective amount of a combination of rapamycin and picibanil. More specifically, the combination reduces tumor size in and prolongs the survival time of transplantable tumor bearing mammals. The combination is useful for treating transplantable tumors selected from the group of lymphocytic leukemia, colon, mammary, melanocarcinoma and ependymoblastoma.

DETAILS OF THE INVENTION

The isolation and description of rapamycin is reported in U.S. Pat. No. 3,929,992, cited above, herein incorporated by reference. Use of rapamycin as an anticancer agent is reported in the above cited U.S. patent application Ser. No. 957,626, filed Nov. 3, 1978, herein incorporated by reference. A composition of rapamycin useful for intravenous injection is described in U.S. patent application Ser. No. 155,250, filed June 2, 1980, herein incorporated by reference.

Rapamycin is administrated to a transplantable tumor bearing mammal for the purpose of reducing the transplantable tumor size and prolonging the survival time of the transplantable tumor bearing mammal, either orally or parenterally, preferably parenterally, e.g. intravenously or interperitoneally.

While rapamycin can be administered above, e.g. as a sole component of a filled capsule, it is preferred to formulate the compound in various dosage forms for oral or parenteral administration, e.g. tablets or sterile solutions. Such formulations are described in U.S. Pat. No. 3,929,992 and U.S. patent application Ser. No. 155,250, both cited above.

When utilizing rapamycin in combination with picibanil for the treatment of transplantable tumors, the total dose of rapamycin can range from 0.5 to 500 mg per kg of body weight per day with a preferred dosage range from 10 to 250 mg per kg of body weight per day. However as the dosage of rapamycin to be administered by the method of this invention will of course vary with the tumor or cancer and tolerance of the mammal, it is preferred to initiate treatment of the transplantable tumor bearing mammal with a low daily dose of rapamycin and then to gradually increase the dosage until a desirable reduction in transplantable tumor size is achieved without causing any harmful or deleterious side effects. The schedule of dosing can range from one to five times per day to a single dose given every two to ten days. Such dosages and scheduling of administration must be determined on an individual basis, depending upon the tumor or cancer, nutritional state of the mammal, age of the mammal, toxicity in each individual, etc.

Rapamycin in combination with picibanil, reduces transplantable in and prolongs the survival time of transplantable tumor-bearing mammals. The efficacy of this combination is greater than the mere addition of the efficacy obtained when rapamycin or picibanil is given alone. Accordingly, the combination is particularly useful for controlling carcinogenic tumors in a mammal. Examples of such transplantable tumors are lymphocytic leukemia, colon, mammary, melanocarcinoma and ependymoblastoma. The effectiveness of the combination in this respect can be demonstrated in the labortory with rodents having transplanted tumors. Details of methods used to evaluate this effect are described in various publications; for example, R. I. Geran et al., Cancer Chemother. Rep., Part 3, 3, (No. 2) 1-103 (1972) and references therein. In addition, protocols for the above antitumor tests are available from the National Cancer Institute, Bethesda, Md., U.S.A. These tests demonstrate that picibanil potentiates the antitumor effect of rapamycin.

The preparation and description of picibanil (OK-432) is given by T. Aoki, cited above. Measurement of the amount of picibanil is expressed in Klinische Einheit (KE), 1 KE contains 0.1 mg dried cocci ($10^7$–$10^8$ cocci). The dosage of picibanil ranges from about 0.1 KE to about 20 KE, preferably from about 0.5 to about 5 KE, per kilogram of body weight per day in a single dose or divided doses; the preferred route of administration of picibanil is by injection of a saline suspension.

The following examples illustrate the use of a combination of rapamycin and picibanil for treating tumors.

EXAMPLE 1

P388 lymphocytic leukemia cells obtained from the National Cancer Institute, Bethesda, Md., U.S.A., are routinely transplanted in male DBA/2J mice purchased from Jackson Laboratories, Bar Harbour, Maine, U.S.A. In the test, $BDF_1$ mice (C57/BL ♂ ×DBA/2 ♀) were used; these mice were specific pathogen-free (SPF) grade animals and weighed 18–23 grams at the beginning of the experiments. On day 0, each mouse received intraperitoneally $1 \times 10^6$ P388 cells, suspended in 0.2 ml of saline, which grew in ascites tumor form. Treatment started on day 1 according to the schedule in Table 1. The rapamycin injectable preparation comprised: 5.5 mg rapamycin, 0.1 mg butylated hydroxyanisole, 75 mg absolute ethanol, 100 mg Cremophor EL and 1 ml (q.s.) water. The picibanil preparation was made by adding 0.66 ml saline to a vial containing 5 KE picibanil. Rapamycin and picibanil were administered intraperitoneally; each group comprised 6 mice. The evaluation parameter was the median survival time (MST), and the results are expressed in T/C% values, which are obtained from the following equation:

$$T/C\% = \frac{MST \text{ (treatment)}}{MST \text{ (control)}} \times 100$$

A T/C% value above 130 is considered significant in the P388 model.

The results are reported in Table 1. As seen from this table, in treatment schedule 1X (single administration on day 1), rapamycin alone showed activity which is not considered significant; in combination with picibanil (4 KE), high significant activity was obtained; picibanil alone (4 KE) was inactive T/C% 105). In treatment schedule 3X (administration on days, 1,5,9), rapamycin alone yielded significant values at 100 mg/kg/injection; in combination with picibanil (1.5 KE/injection), rapamycin showed much higher activity at all doses tested (25–100 mg/kg/injection); picibanil alone was not significantly active (T/C% 110). In the treatment schedule 9X (administration on days 1 to 9), rapamycin alone was significantly active at 12.5–50 mg/kg/injection: picibanil alone (0.5 KE/injection) also was significantly active; rapamycin and picibanil in combination showed much higher activity than when given alone. In conclusion, the combination of rapamycin and picibanil is always more potent than each compound given alone. In treatments 1X, 3X and 9X picibanil potentiated the anti-P388 lymphocytic leukemia activity of rapamycin.

EXAMPLE 2

In a separate experiment performed as in Example 1 (treatment on days 1 and 5), the evaluation parameter was P388 cell growth (instead of MST). Animals (3/group) were sacrificed on days 0,1,5,9 and their peritoneal cavity washed with saline to recover the P388 cells, which were counted immediately in haemacytometer under the microscope. The results are shown in Table 2, wherein results on day 5 indicate that picibanil alone encourages the proliferation of P388 cells, which corroborates the results of Table 1 (treatment schedules 1X and 9X) that picibanil is inactive in these conditions. Rapamycin, given alone, slows P388 cell proliferation significantly. The results on day 9 indicate the picibanil, in combination with rapamycin, increased the inhibiting effect of rapamycin. In conclusion, the combination of rapamycin plus picibanil is more potent than each compound given alone in inhibiting P388 cell proliferation; the effect is more pronounced with the passage of time.

TABLE 1

The effect of rapamycin and picibanil, given alone and in combination, on survival time of $BDF_1$ mice with P388 lymphocytic leukemia

| Rapamycin doses (mg/kg/injection) | 1X, on day 1 | | 3X, on days 1, 5, 9 | | 9X, from day 1 to 9 | |
|---|---|---|---|---|---|---|
| | Rapamycin alone | Rapamycin + Picibanil 4KE | Rapamycin alone | Rapamycin + Picibanil 1.5KE | Rapamycin alone | Rapamycin + Picibanil 0.5KE |
| Vehicle control (MST) | 10.5 days | 10.0 days | 10.5 days | 10.5 days | 11.5 days | 10.5 days |
| 200 | 124 | 160 | — | — | — | — |
| 100 | 129 | 160 | 148 | 190 | — | — |
| 50 | 114 | 155 | 129 | 162 | 148 | 205 |
| 25 | — | — | 124 | 167 | 148 | 205 |
| 12.5 | — | — | — | — | 148 | 210 |
| 0 | — | 105 | — | 110 | — | 167 |

TABLE 2

The effect* of rapamycin and picibanil, given alone and in combination, on P388 lymphocytic leukemia cell growth

| Treatment | Days after tumor cell inoculation | | | |
|---|---|---|---|---|
| | 0 | 1 | 5 | 9 |
| No treatment | | | $77 \times 10^6$ | $470 \times 10^6$ |
| Vehicle control | | | $84 \times 10^6$ | $447 \times 10^6$ |
| Picibanil, 1.5 KE | $1 \times 10^6$ | $.66 \times 10^6$ | $137 \times 10^6$ | $440 \times 10^6$ |
| Rapamycin, 200 mg/kg | | | $3.5 \times 10^6$ | $75 \times 10^6$ |
| Picibanil, 1.5 KE and Rapamycin, 200 mg/kg | | | $7.2 \times 10^6$ | $8.7 \times 10^6$ |

*Expressed as number of tumor cells per mouse.
Treatments were given on Day 1 and Day 5.

1 claim:

1. A method of reducing tumor size in a tumor bearing mammal or prolonging the survival time in a tumor bearing mammal, wherein said tumor is a transplantable tumor selected from the group consisting of lymphatic leukemia, colon, mammary, meleanocarcinoma and ependymoblastoma, which comprises administering to said mammal an antitumor effective amount of a combination of rapamycin and picibanil, said rapamycin being administered at a daily dose of from 10 to 250 mg per kg of body weight and said picibanil being administered at a daily dose of 0.5 to 5 KE per kg of body weight.

2. The method of claim 1 wherein said tumor is lymphocytic leukemia.

3. The method of claim 1 wherein rapamycin and picibanil are administered parenterally.

4. The method of claim 1 wherein rapamycin and picibanil are administered sequentially or simultaneously.

* * * * *